US00PP13855P39

(12) United States Plant Patent
Kos

(10) Patent No.: US PP13,855 P3
(45) Date of Patent: Jun. 3, 2003

(54) LILY PLANT NAMED 'YELLOWEEN'

(75) Inventor: Pieter Jan Kos, Anna Paulowna (NL)

(73) Assignee: World Breeding, B.V. (NL)

( * ) Notice: Subject to any disclaimer, the term of this patent is extended or adjusted under 35 U.S.C. 154(b) by 0 days.

(21) Appl. No.: 09/834,758

(22) Filed: Apr. 13, 2001

(65) Prior Publication Data

US 2002/0152529 P1 Oct. 17, 2002

(51) Int. Cl.[7] ..... A01H 5/00
(52) U.S. Cl. ..... Plt./313
(58) Field of Search ..... Plt./313

(56) References Cited

PUBLICATIONS

The Royal Horticultural Society Dictionary of gardening, The Royal Horticultural Society, 1992, pp. 68–80.*

* cited by examiner

*Primary Examiner*—Bruce R. Campell
*Assistant Examiner*—Anne Marie Grünberg
(74) *Attorney, Agent, or Firm*—Klarquist Sparkman LLP

(57) ABSTRACT

A new and distinct variety of upright Oriental×Aurelia hybrid lily plant, named 'Yelloween' characterized by large, upright, yellow flowers.

1 Drawing Sheet

LATIN NAME OF THE GENUS AND SPECIES OF THE PLANT CLAIMED

Genus: Lilium. Species is unknown.

VARIETY DENOMINATION

'YELLOWEEN'.

BACKGROUND OF THE INVENTION

The present invention relates to a new and distinct variety of Lilium hybrid referred to commercially as an upright Oriental×Aurelia hybrid lily and given the cultivar name 'Yelloween'.

This new variety is the product of a controlled breeding program using embryo culture and was carried out in the municipality of Breezand, The Netherlands, using the proprietary Oriental type hybrid lily 91.30.00-2 as the seed parent and the proprietary Aurelia type hybrid lily 90.058-1 as the pollen parent. The resulting plants were evaluated for cut flower production. Compared to the typical characteristics of common Oriental and Aurelia lily hybrids, 'Yelloween' has larger flowers, taller plant height and taller stems, and blooms earlier.

This new variety has not been observed under all possible environmental conditions. The phenotype may vary significantly with variations in environment such as temperature, light intensity, day length, and nutrient availability, without, however, any variations in genotype.

BRIEF SUMMARY OF THE INVENTION

The following traits have been repeatedly observed and are determined to be the basic characteristics of this invention that, in combination, distinguish this lily as a new and distinct variety:

1. floriferous habit;
2. large upright yellow flowers;
3. vigorous growth habit;
4. tall plant; and
5. excellent vase-life.

Bulbs of this plant may be pre-cooled and forced out of season for very uniform cut flower production.

The primary distinguishing feature of 'Yelloween' is its numerous, large, upright, yellow flowers. The seed parent, an Oriental type hybrid, does not produce yellow flowers. Additionally, 'Yelloween' can be bred approximately 20 days later than the seed parent. The pollen parent, an Aurelia type hybrid, has a different influorescence, and smaller, calyx-like flowers, compared to 'Yelloween.'

Asexual reproduction of this new variety has been accomplished at a nursery in Breezand, The Netherlands, by scaling and tissue culture. The resulting plants have shown that the above-mentioned unique features are stable and reproduce true to type in each successive propagation.

BRIEF DESCRIPTION OF THE DRAWING

This new variety of lily plant is illustrated in the accompanying photographic drawing which shows the upper half portion of the flowering stem of a potted plant in the full face view of the flowers together with some foliage. The accompanying photograph, showing 'Yelloween', was taken in a studio and illustrates the typical flower and foliage form, with color as true as reasonably possible in this type of color illustration.

DETAILED BOTANICAL DESCRIPTION

This detailed description of the 'Yelloween' variety is based on plants approximately 80–90 days old produced in greenhouses in Breezand, The Netherlands. Bulbs were planted in (and the resulting plants were cultivated in) trays with peatmoss. Plants were grown at a minimum temperature of about 15° C. without supplemental fertilization or supplemental lighting. Color references are provided according to The R.H.S. Colour Chart published by The Royal Horticultural Society of London, England, except where the context indicates a term having its ordinary dictionary meaning.

Origin: Resulting from a hybridization.

Parentage:

*Seed parent.*—Oriental type hybrid lily 91.30.00-2 (proprietary owned).

*Pollen parent.*—Aurelia type hybrid lily 90.058-1 (proprietary owned).

Commercial classification: Upright Oriental×Aurelia hybrid lily, cut flower type.

Classification: Division VIII, all hybrids not provided for in any previous Division according to the Horticultural Classification of Lilies by The Royal Horticultural Society.

Form: Single erect stem from each bulb bearing terminal cluster of flowers.

*Height.*—To about 160 cm. from the top of the soil to the top of the inflorescence from bulbs of about 16 to 18 cm. in circumference.

Stem: Color is Green Group (RHS 138B) ascending to Green Group (RHS 137D).

Growth: Vigorous, upright, and strong. Plants grew about 120 cm. over the span of about 80 to 90 days.

Foliage:

*Arrangement.*—Incremental and staggered around the stem.

*Quantity.*—Many fine leaves, with approximately 35 to 40 leaves per plant.

*Leaf size.*—Variable, lower leaves on the stem about 10.5 cm. long and about 4 cm. wide; upper leaves on the stem about 19.5 cm long and about 3 cm wide.

*Leaf shape.*—Lower leaves: Lanceolate. Upper leaves: Round top and wide-shaped.

*Leaf margin.*—Entire.

*Aspect.*—Satiny.

*Texture.*—Leathery.

*Color.*—Upperside of leaves: Green (RHS 139A). Underside of leaves: Green (RHS 138B). Leaf venation: Yellow-green (RHS 144B).

Bulb:

*Type.*—Concentric.

*Size.*—About 5.5 to 6.0 cm. in diameter and about 16 to 18 cm. in circumference.

*Color.*—Yellow-white (RHS 158C).

Bud:

*Size.*—To about 12 cm. long and to about 3 cm. wide, just prior to opening.

*Shape.*—Lanceolate, with the apex commonly having three obtuse tips.

*Color.*—At first opening, the color is Yellow (RHS 5C), turning Yellow (RHS 6A) when unfurling.

*Opening rate.*—The mature bud opens slowly in response to light.

Flower:

*Blooming habit.*—Annually, once and profusely.

*Days to bloom.*—Flowers approximately 80 days after greenhouse planting under typical flower forcing conditions at minimum temperature of 15° C.

*Outdoor blooming time.*—Bulbs planted in March flower about mid-July.

*Greenhouse blooming time.*—Bulbs can be planted year-round and forced to bloom approximately 80 to 90 days after planting. Greenhouse bloom lasts about 12 to 15 days.

*Flower number.*—Approximately 5 to 7 flowers per plant.

*Flower size.*—Large.

*Diameter.*—To about 23 cm.

*Depth.*—To about 7 cm.

*Borne.*—Raceme of about 3 flowers from bulbs of about 16 to 18 cm. in circumference.

*Shape.*—The flower is funnel shaped, later the funnel flattens out.

*Tepalage.*—Number: 6. Arrangement: Imbricated. Shape: Oval. Texture: Leathery. Aspect: Glossy. Size: Length: Inner tepals to about 14 cm. Outer tepals to about 14.3 cm. Width: Inner tepals to about 6 cm. Outer tepals to about 4 cm. Nectary: Light Green (RHS 144A) from base. Oozing to about 2 cm. Spots: None. Blush: None. Color: Outer tepals: Abaxial: Yellow (RHS 6A). Adaxial: Yellow (RHS 5C). Inner tepals: Abaxial: Yellow (RHS 6A). Adaxial: Yellow (RHS 5C). Fragrance: Weak.

*Lasting quality.*—Excellent. Each flower lasts about 14 days, with a vase life of about 12 to 15 days. Orientation: Ascending upwardly off the stem, the first flower at about a 30° angle to about a 35° angle.

*Pedicel.*—Length: About 14 cm. Color: Green (RHS 137C).

Reproductive Organs:

*Stamens.*—Number: Six, typical of the genus Lilium.

*Anthers before dehiscense.*—Size: To about 4.3 cm. from mature bud. Color: Dark Purple (RHS 187A).

*Filaments.*—Length: To about 8.4 cm. Color: Yellow-Green (RHS 145C).

*Pollen.*—Color: Brown (RHS 183A).

*Pistil.*—Number: One.

*Style.*—Length: About 8 cm. Color: Light Green (RHS 145C).

*Stigma.*—Color: Light Green (RHS 149C).

Fruit:

*Fertility.*—Fruit is produced.

*Shape.*—Ovoid.

*Color at maturity.*—Brown Green (RHS 152B).

*Fungal resistance.*—Some resistance to Pytium species.

I claim:

1. A new and distinctive variety of Oriental×Aurelia hybrid lily plant, substantially as herein illustrated and described.

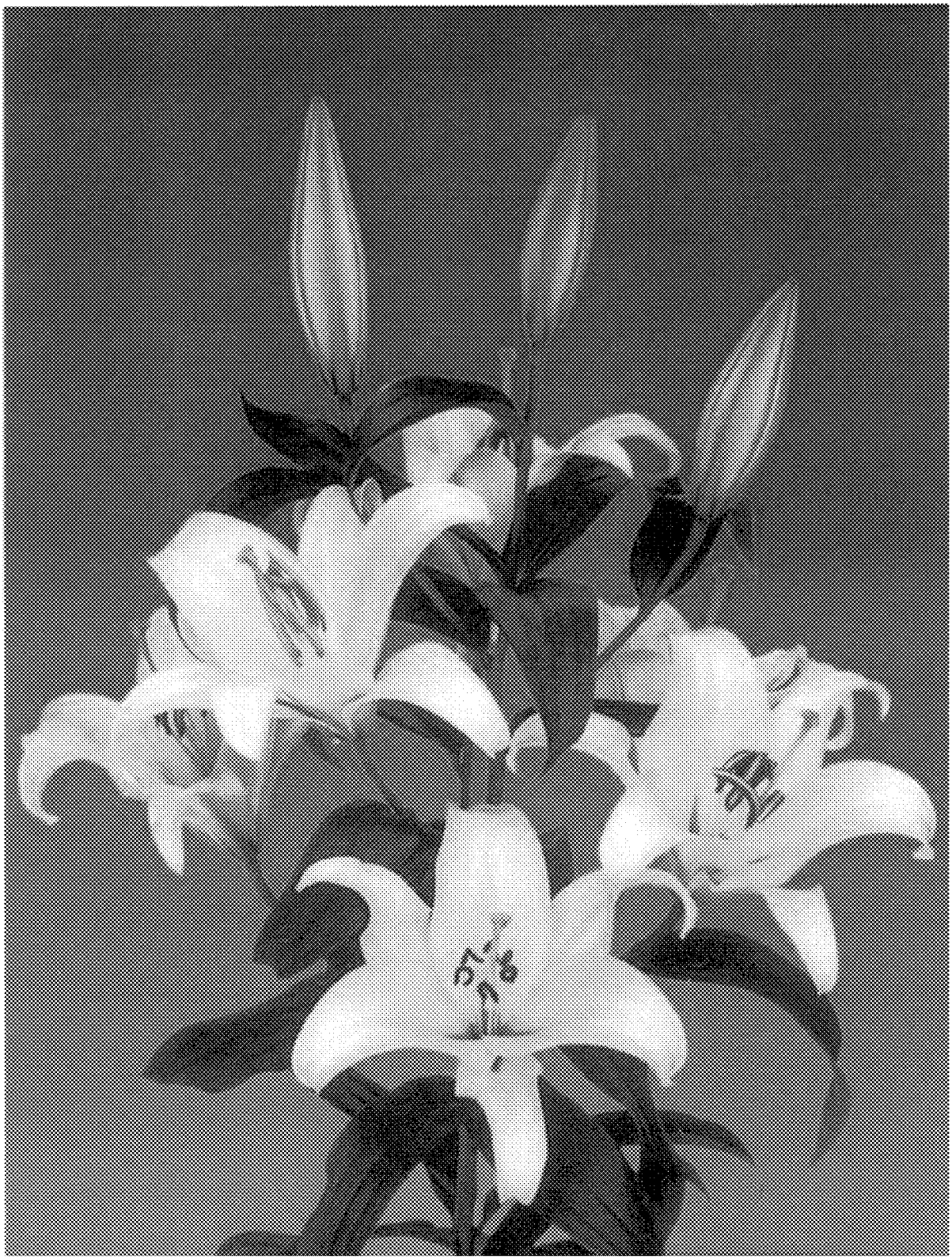

* * * * *